US011771413B2

(12) United States Patent
Rajek

(10) Patent No.: US 11,771,413 B2
(45) Date of Patent: Oct. 3, 2023

(54) RETRACTOR BLADE DEVICES AND RELATED METHODS

(71) Applicant: Alphatec Spine, Inc., Carlsbad, CA (US)

(72) Inventor: Andrew W. Rajek, Escondido, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 0 days.

(21) Appl. No.: 17/563,520

(22) Filed: Dec. 28, 2021

(65) Prior Publication Data

US 2022/0202404 A1 Jun. 30, 2022

Related U.S. Application Data

(60) Provisional application No. 63/131,707, filed on Dec. 29, 2020.

(51) Int. Cl.
*A61B 17/02* (2006.01)
(52) U.S. Cl.
CPC .... *A61B 17/025* (2013.01); *A61B 2017/0256* (2013.01)
(58) Field of Classification Search
CPC .......... A61B 17/025; A61B 2017/0256; A61B 17/02
USPC ................................................. 600/184–245
See application file for complete search history.

(56) References Cited

U.S. PATENT DOCUMENTS

| | | | |
|---|---|---|---|
| 9,770,236 B2* | 9/2017 | Stauber | A61B 17/8866 |
| 10,070,852 B2 | 9/2018 | Mast | |
| 10,172,515 B2 | 1/2019 | Lee | |
| 10,695,044 B2 | 6/2020 | Miles | |
| 2005/0149035 A1* | 7/2005 | Pimenta | A61B 17/02 606/86 R |
| 2007/0198062 A1 | 8/2007 | Miles | |
| 2012/0296171 A1* | 11/2012 | Lovell | A61B 17/025 600/213 |
| 2014/0221760 A1 | 8/2014 | Perrow | |
| 2018/0055504 A1* | 3/2018 | Mast | A61B 17/0206 |
| 2018/0271513 A1* | 9/2018 | Perrow | A61B 17/0293 |

OTHER PUBLICATIONS

European Patent Office, acting as International Searching Authority, "International Search Report and Written Opinion," International Application No. PCT/US2021/065356, dated Apr. 4, 2022.

\* cited by examiner

*Primary Examiner* — Eduardo C Robert
*Assistant Examiner* — Tara Rose E Carter
(74) *Attorney, Agent, or Firm* — Robert Winn

(57) ABSTRACT

Disclosed herein are retractor blade devices, such as blade extenders and tissue shims, as well as drivers and kits for utilizing such retractor blade devices. Exemplary retractor blade devices include a retractor blade engagement portion having a body portion configured to sit at least partially in a channel of a retractor blade. The body portion has a first retention component extending therefrom. Exemplary retractor blade devices also include an extension portion extending from the body portion of the retractor blade engagement portion.

20 Claims, 8 Drawing Sheets

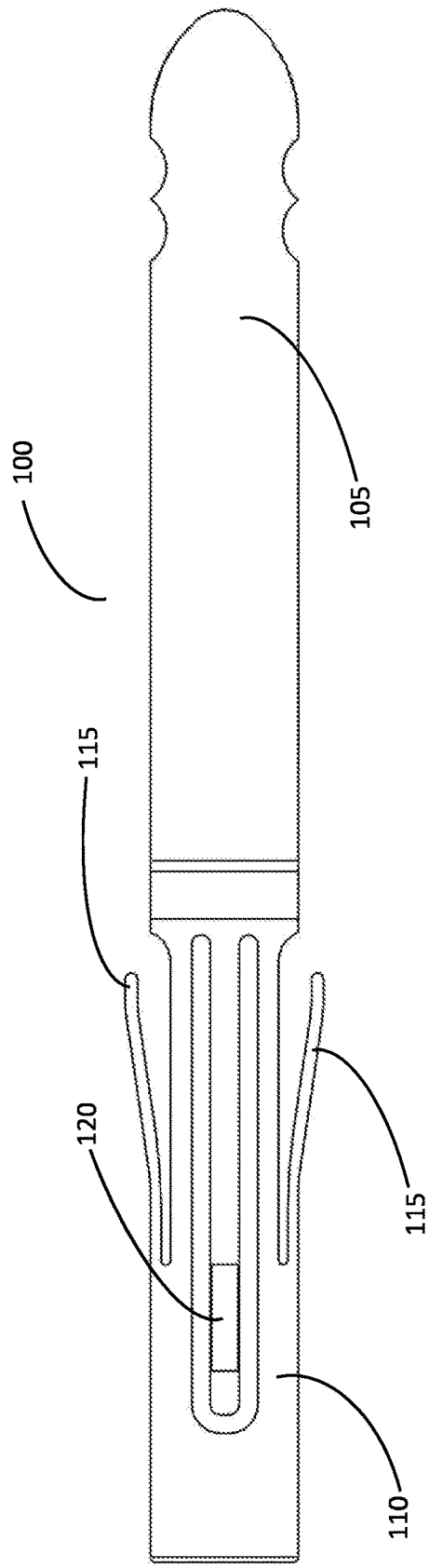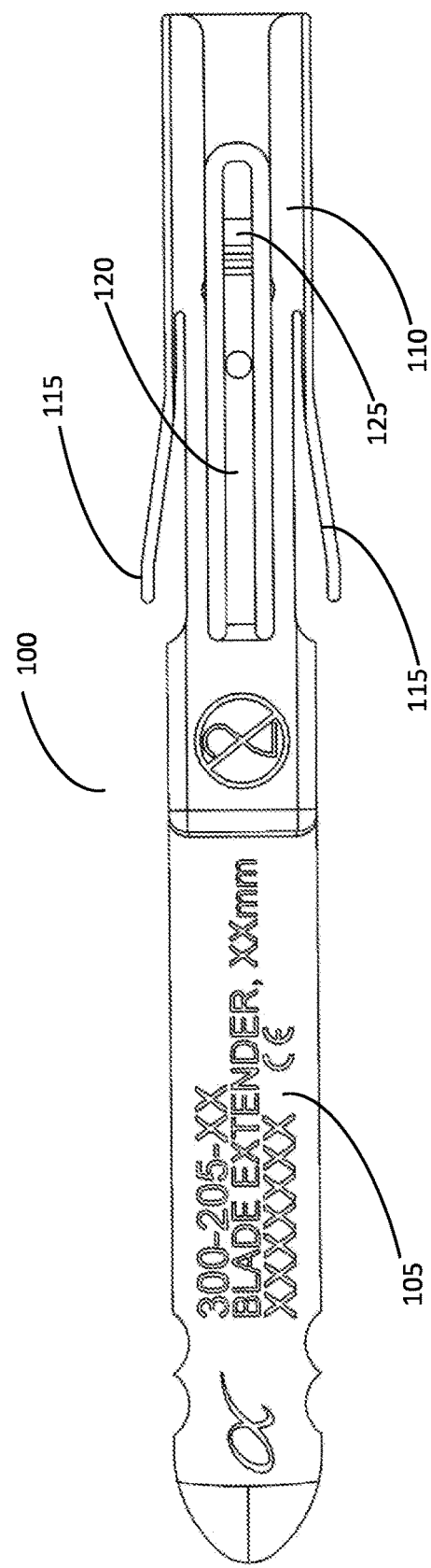
FIG. 3A
FIG. 3B

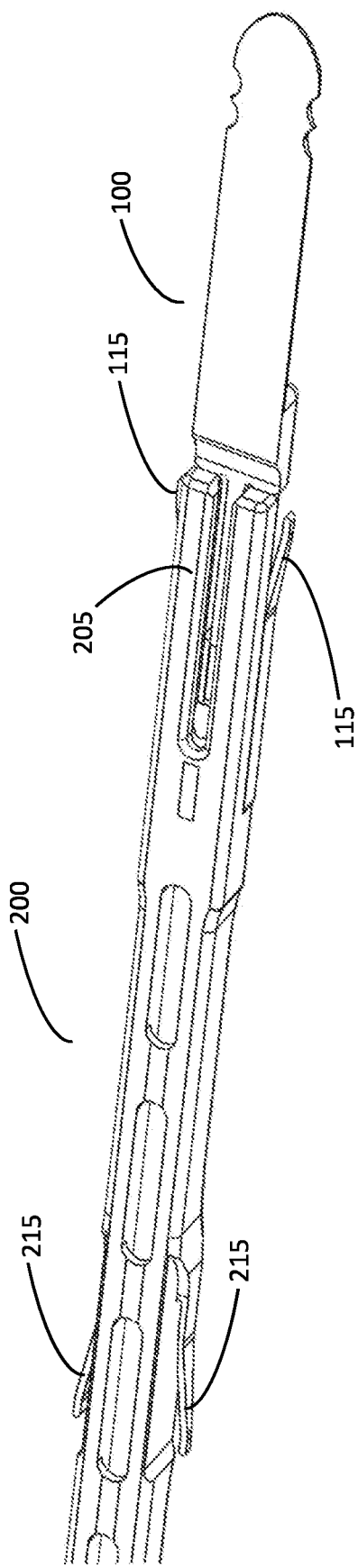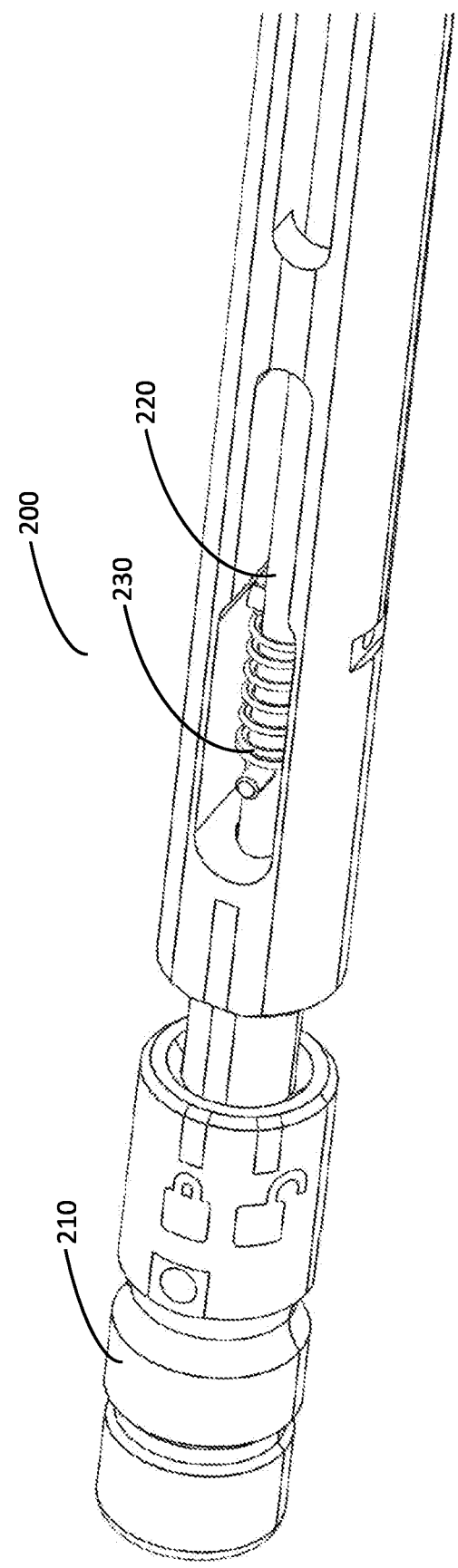
FIG. 4A
FIG. 4B

RETRACTOR BLADE DEVICES AND RELATED METHODS

CROSS-REFERENCE TO RELATED APPLICATIONS

This application claims priority to U.S. Provisional Application No. 63/131,707, filed Dec. 29, 2020, the entire contents of which are incorporated herein by reference.

FIELD OF THE TECHNOLOGY

The present disclosure generally relates to medical devices for retracting tissue and creating and maintaining a surgical corridor. In particular, disclosed herein are embodiments of an instrument that may be used to help create and maintain a surgical corridor that can also be secured to the blade of a surgical retractor positioned in the surgical corridor.

BACKGROUND

Retractor systems may be used in a variety of different surgical procedures to provide an opening through which a surgeon may access the surgical site. In spinal surgeries, for example, a retractor system may be used to provide the surgeon with access to the patient's spine. The opening created by the retractor system may, for example, enable the surgeon to access the patient's spine to manipulate the spine and secure implants in or on the spine. Common retractor systems may include a plurality of blades coupled to a retractor frame. In use, the blades may be inserted into an incision and then retracted to displace tissue surrounding the incision down to the surgical site thereby creating a surgical corridor. However, despite the ability to maneuver the blades of some retractor systems, there still exists a need for further manipulation of the tissue particularly after the blades have achieved an initial surgical corridor.

SUMMARY

Disclosed herein are various devices largely for use with surgical retractor blades. Such devices comprise a retractor blade engagement portion and extension or working portion. The engagement portion is configured to be releasably engaged in a channel or track of the retractor blade. The extension or working portion may be shaped or designed to achieve any number of functions, such as but not limited to, the functions of a tissue shim, an intradiscal shim, a blade extender, etc.

According to some embodiments, the retractor blade engagement portion has a body portion with a distal end and a proximal end, and the retractor blade engagement portion is configured to sit at least partially in a channel of a retractor blade. The body portion has at least one retention component extending therefrom configured to engage the channel or track of the retractor blade. Some embodiments have two retention components.

The extension portion may be substantially flat or curved. The extension portion may include a hook feature. The extension portion may be wider than the retractor blade engagement portion. At least a portion of the extension portion may extend laterally of the blade engagement portion. The distal end of the extension portion may extend beyond the distal end of the blade engagement portion by at least about 0.1 cm, at least about 1 cm, at least about 2 cm, at least about 3 cm, or at least about 4 cm. The proximal end of the extension portion may be positioned at any one of the following positions relative to the proximal and distal ends of the blade engagement portion: (a) proximally of the proximal end; (b) substantially in line with the proximal end; or (c) at a point between the proximal and distal ends.

According to some embodiments, the body portion defines a first plane and the extension portion defines a second plane. The first and second planes may be parallel to each other. The first and second planes may not be coplanar.

According to some embodiments, the retention component(s) comprise(s) a resilient projection. The retention component(s) may extend(s) in a plane coplanar with the body portion. The retention component(s) is (are) configured to allow the retractor blade device to be brought into the retractor blade channel from a position perpendicular to a plane defined by the channel.

According to some embodiments, the distal end of the extension portion has a rounded profile. The extension portion may include at least one scalloped edge.

According to some embodiments, the body portion includes a driver locking mechanism. The driver locking mechanism may include a resilient portion and a projection. The projection may be configured to engage a depression in the retractor blade. The resilient portion may lie substantially in the same plane as the body portion and may extend from a plane defined by the body portion.

According to some embodiments, the extension portion comprises a channel or track extending from a point near the proximal end of the extension portion toward the distal end of the extension portion. The channel or track may be open at its proximal end and/or open at its distal end.

Also disclosed herein device drivers configured to engage a retractor blade device as disclosed herein. Such drivers include a handle, an elongate housing, a shaft contained within the housing, and a receiving portion configured to receive at least a portion of the retractor blade device. The handle is configured to communicate with the shaft to releasably engage the retractor blade device. The receiving portion may be a distal opening in the housing configured to receive at least a portion of the body portion of the retractor blade device.

According to some embodiments, the blade device driver is configured to releasably engage the driver locking mechanism of the retractor blade device. The housing comprises at least one retention component configured to retain the blade device driver in a channel of a retractor blade. Some embodiments include two retention components. The retention component(s) may be configured to allow the blade device driver to be brought into the channel from a position perpendicular to a plane defined by the channel. The handle may be configured to occupy a locked position that allows compaction forces to be transferred from the handle through the housing and directly to the retractor blade device.

Also disclosed herein are retractor blade kits that include a retractor blade and a retractor blade device, such as those disclosed herein. The retractor blade may define a plane and has a proximal end and a distal end and includes a channel extending from the proximal end toward the distal end. The retractor blade device is configured to be engaged with the channel by inserting at least a portion of the retractor blade device into the channel at a point away from the proximal end of the retractor blade.

According to some embodiments of retractor blade kits, the channel is closed at the distal end of the retractor blade. The channel may be open at the proximal end of the retractor blade. The retractor blade device may be further configured to be engaged with the channel by inserting at least a portion of the retractor blade device into the channel by accessing the opening of the channel at the proximal end of the retractor blade. Some embodiments further include a blade device driver configured to engage with at least a portion of the retractor blade device. The blade device driver may be further configured to manipulate the movement of the retractor blade device and engage the retractor blade device with the channel of the retractor blade.

Also disclosed herein are methods of using a retractor blade device in conjunction with a surgical retractor having at least one or more retractor blades. Such methods include engaging the retractor blade device with a channel of a retractor blade by inserting at least a portion of the retractor blade device into the channel at a point distal to a proximal end of the channel. Engaging the retractor blade device with the channel of the retractor blade may comprise moving at least a portion of the retractor blade device in a direction normal to a plane defining the channel. Engaging the retractor blade device with the channel of the retractor blade may comprise engaging at least a portion of the retractor blade device with one or more depressions in the channel of the retractor blade. The retractor blade may be positioned within a surgical opening of a patient so as to create a surgical corridor prior to the retractor blade device being engaged with the channel on the retractor blade. Some methods further include sweeping the surgical corridor and/or a surgical site of interfering tissue with the retractor blade device prior to the retractor blade device being engaged with the channel of the retractor blade. Some methods include the use of a blade device driver to insert the retractor blade device into the surgical corridor, manipulate the movement of the retractor blade device in the surgical corridor, and/or engage the retractor blade device with the channel of the retractor blade. Some methods further include toeing out the retractor blade while simultaneously advancing the retractor blade device distally along the channel of the retractor blade. Some methods further include detaching the blade device driver from the retractor blade device so as to leave the retractor blade device in the channel of the retractor blade while removing the blade device driver from the surgical corridor. Removing the blade device driver from the surgical corridor may include sliding the blade device driver proximally along the channel of the retractor blade and out a proximal opening of the channel.

These and other features are disclosed in greater detail in the accompanying figures and the Detailed Description below.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings wherein like structure is indicated with like reference numerals and in which:

FIGS. 3A & 3B are front and back views, respectively, of the retractor blade device of FIG. 1A;

FIG. 4A is a perspective view of the retractor blade device of FIG. 1A coupled to a driver.

FIG. 4B is a perspective view of a portion of the driver of FIG. 4A.

DETAILED DESCRIPTION

Disclosed herein are devices that augment or enhance the functionality of some retractor blades. Such devices may be referred to as retractor blade extenders and may be used with drivers to help control or manipulate the extenders or other enhancement devices. Also disclosed are methods of using such enhancement devices to enlarge, restore, and/or maintain a surgical corridor. These enhancement devices are removably attached to retractor blades. Such devices may be used to pull back and maintain tissue that has crept into a surgical corridor. Such devices may be used to functionally increase the size of the retractor blade, thereby increasing the amount of tissue that can be held in place. Such devices may be used to temporarily anchor the retractor blade relative to a disc space.

Figure 1A:
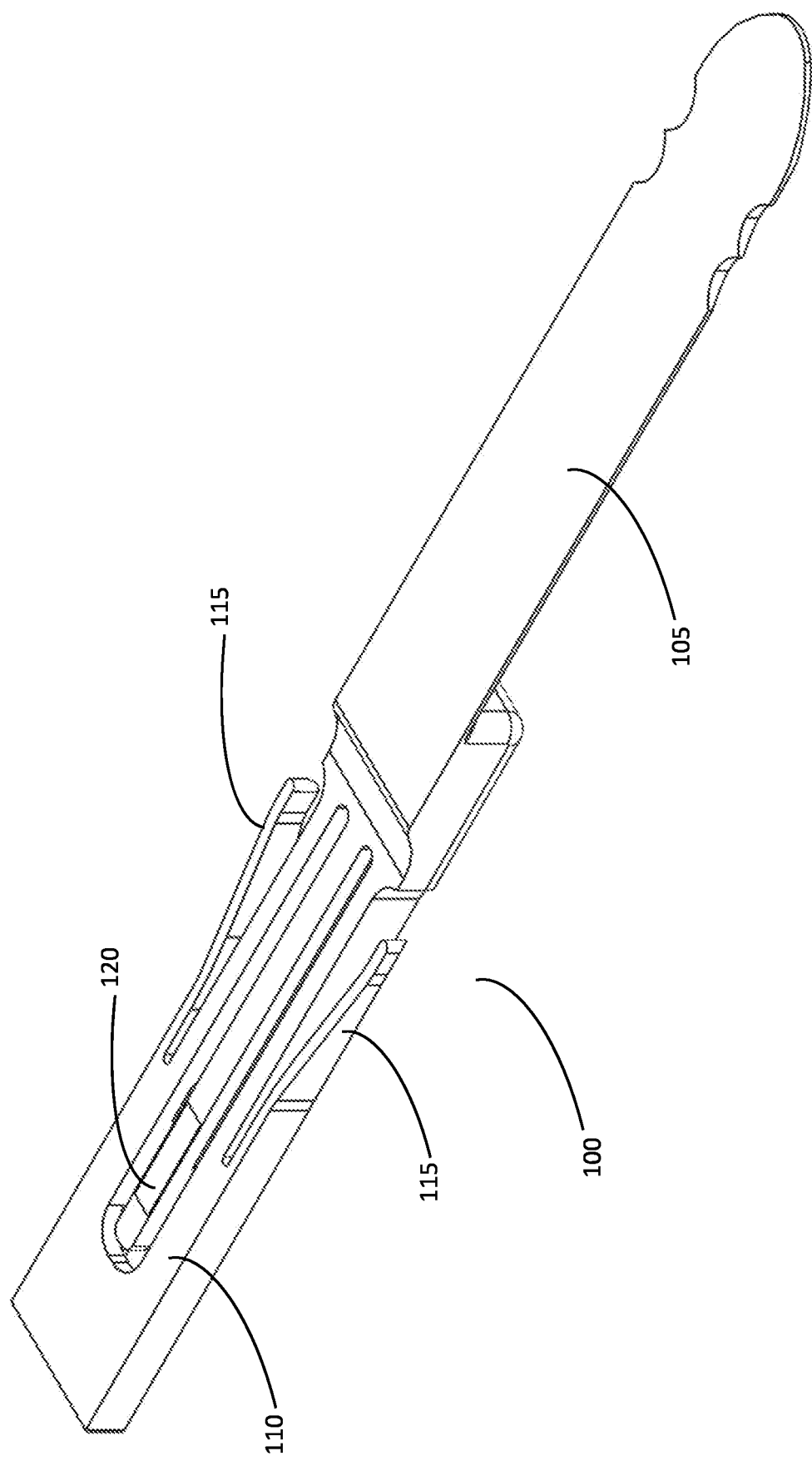
FIGS. 1A and 1B are perspective views of an embodiment of a retractor blade device according to the present disclosure.
Figure 1B:
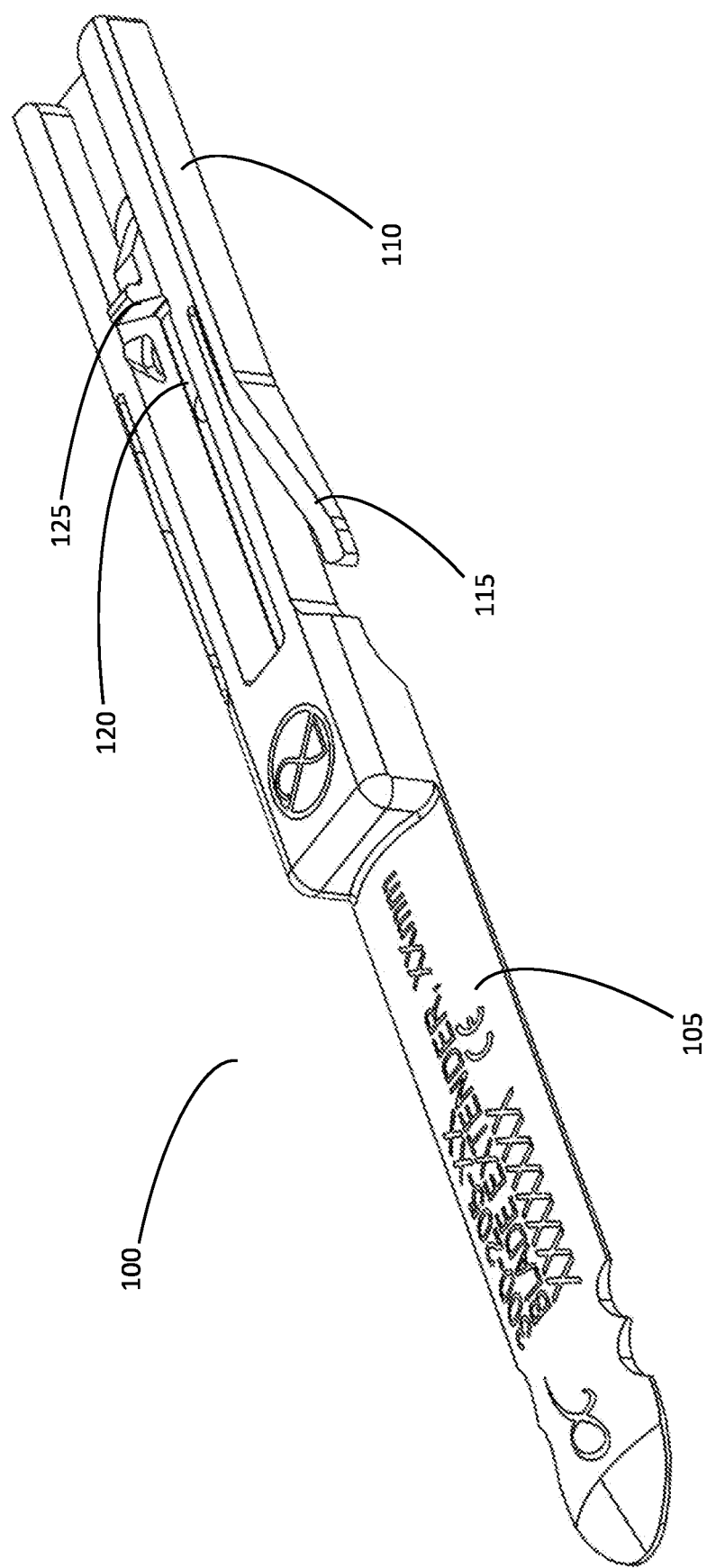

FIGS. 1A and 1B illustrate perspective views of one such enhancement device, a retractor blade extender 100, according to the present disclosure. Retractor blade extender 100 may be referred to herein as a blade extender or simply an extender. A skilled artisan will understand that the features of blade extender 100 discussed herein could be applied to any number of suitable enhancement devices, such as a tissue shim or a tissue hook, etc. as discussed below.

Figure 5A:
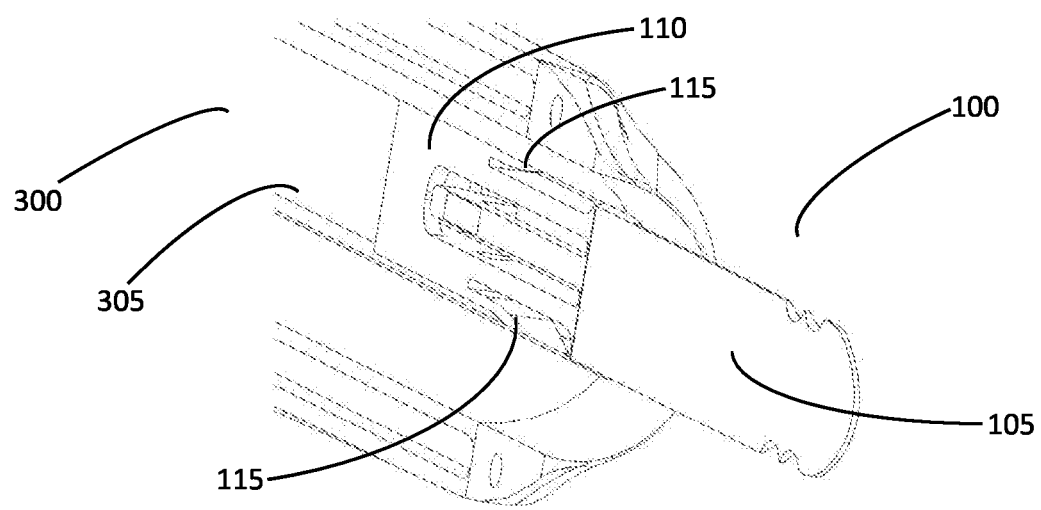
FIG. 5A is a perspective view of the distal end of a retractor blade with the retractor blade device of FIG. 1A secured therein.
Figure 5B:
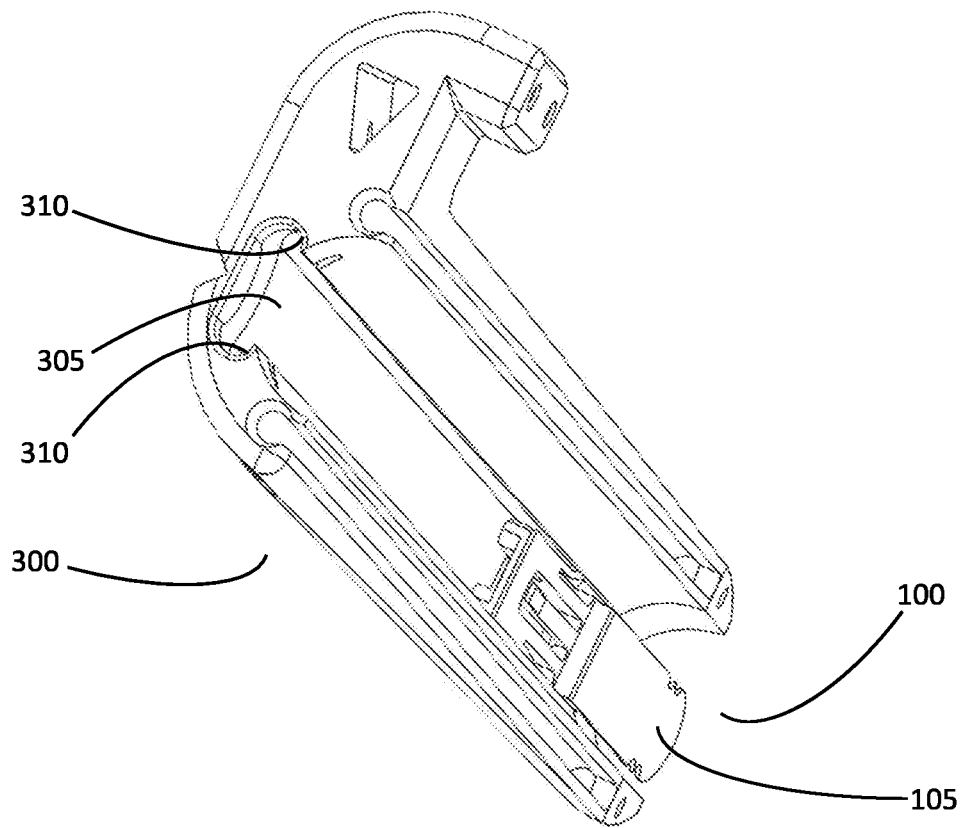
FIG. 5B is a perspective view of the retractor blade of FIG. 5A with the retractor blade device of FIG. 1A secured therein.

Blade extender 100, as illustrated, has both an extension portion 105 and a blade engagement portion 110, sometimes called a driver engagement portion, where blade engagement portion 110 is configured to be secured in and, and in some embodiments, translate along a channel of a retractor blade, such as that shown in FIGS. 5A and 5B. In some embodiments, blade engagement portion 110 is further configured to lock in place in the retractor blade channel.

Extension portion 105 comprises an elongate body that is relatively flat like a blade, the distal end of which is rounded, which may help when inserting blade extender 100 into a surgical corridor and/or when blade extender is used to push or pull tissue away from the surgical site and hold it back as will be discussed in greater detail below. Elongate portion 105 may have blade-like edges with a portion of the edge on either side being scalloped and/or serrated, as illustrated. In some embodiments, the edges of elongate portion 105 are sharp enough to allow for elongate portion to be at least partially inserted into a disc space, for example, to serve as a temporary anchor for a retractor blade. In some embodiments, the edges of elongate portion 105 are not so sharp as to undesirably sever tissue in the surgical corridor.

FIG. 1A illustrates that elongate portion 105 and blade engagement portion 110 each define a plane. In this illustrated embodiment and in others, the respective planes are parallel to each other but no coplanar. This offset between elongate portion 105 and blade engagement portion 110 may provide a bottoming out feature when paired with a retractor blade. In other words, when blade engagement portion 110 is secured in a channel of a retractor blade, if that channel has a closed distal end, blade engagement portion 110 will extend no further than that closed distal end; however, elongate portion 105 will extend beyond the distal end of the channel and, in some embodiments, beyond the distal end of the retractor blade (as illustrated in FIG. 5A). However, in some embodiments, blade engagement portion 110 and elongate portion 105 are coplanar, and in some embodiments—whether or not coplanar—the respective planes defined by blade engagement portion 110 and elongate portion 105 are not parallel but exhibit a slight angle between them or, in some embodiments, a substantial angle.

Elongate portion 105 is illustrated as being relatively flat; however, in some embodiments elongate portion 105 exhibits a curvature, such as a curvature corresponding to the shape of the surgical corridor.

Figure 2B:
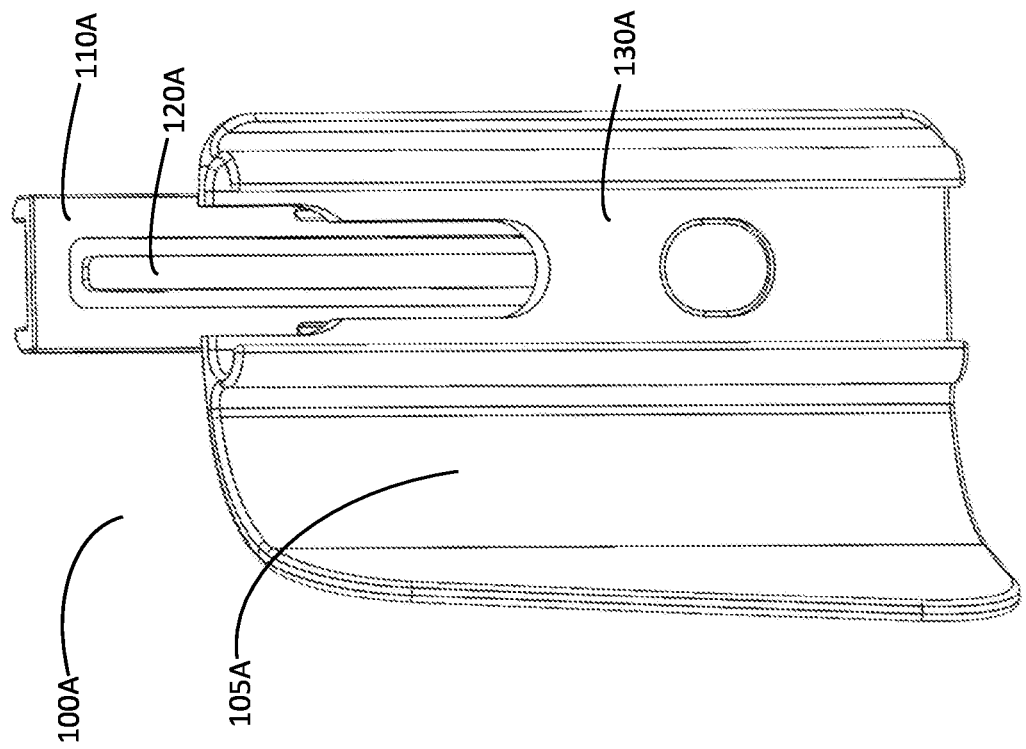
FIGS. 2A and 2B rear and front views of another embodiment of a retractor blade device according to the present disclosure.
Figure 2A:
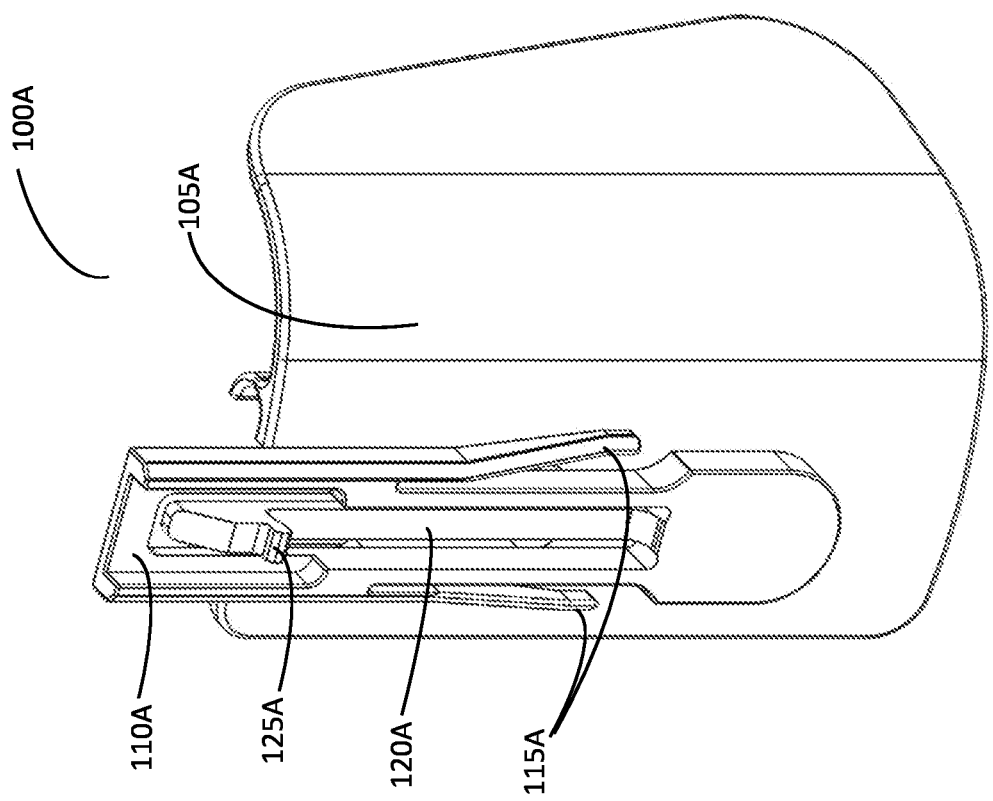

FIGS. 2A and 2B illustrate one variation on blade extender 100, which may be referred to as a tissue shim 100A. Similar to blade extender 100, tissue shim 100A includes a blade engagement portion 110A having two engagement tabs 115A and a locking tab 120A with a projection 125A. The function of these features will be largely similar to the function of the corresponding features of blade extender 100 as discussed herein as would be readily apparent to a skilled artisan. However, tissue shim 100A includes a shim portion 105A that differs from elongate portion 105 not only in that it does not extend as far beyond blade engagement portion 110A but also because of the lateral surfaces that extends well beyond the lateral edge of blade engagement portion 110A and includes a substantial curvature. Shim portion 105A could be located on either side or on both sides of blade engagement portion 110A and could exhibit any number of different shapes and curvatures as may be desired for specific needs and surgical procedures.

FIG. 2B illustrates that tissue shim 100A further includes an auxiliary channel 130A that may be used in lieu of the channel of the retractor blade that is occupied with tissue shim 100A. Additionally, auxiliary channel 130A is shown as extending beyond the distal end of blade engagement portion 110A. Thus, auxiliary channel 130A may serve to create a functional channel further into the surgical corridor and, therefore, closer to the surgical site. In some embodiments, auxiliary channel 103A may be used by blade extender 100, thereby functionally combining both tissue shim 100A and blade extender 100.

Returning to blade extender 100, FIGS. 3A and 3B illustrate elongate portion 105 as having substantially the same width as blade engagement portion 110; however, in some embodiments, elongate portion 105 is substantially wider than blade engagement portion 110 so as to provide a greater surface area against the encroachment of tissue into the surgical corridor. In such embodiments, elongate portion 105 does not extend much beyond the distal end of the retractor blade, and the increased width may not necessarily be centered relative to the retractor blade. For example, one lateral side of the elongate portion 105 may extend outwardly greater than the opposite lateral side of the elongate portion 105 such that the width of the elongate portion is not centered relative to the retractor blade.

Elongate portion 105 and blade engagement portion 110 may comprise the same materials or distinct materials. For example, in some embodiments, it is desirable for elongate portion 105 to exhibit some flexibility, whereas engagement portion 110 may need to exhibit less flexibility so as to provide a solid engagement with a retractor blade channel.

Blade engagement portion 110 includes two complimentary extensions or blade engagement tabs 115 that extend laterally from each side of blade engagement portion 110. In some embodiments, engagement tabs 115 lie in the same plane as blade engagement portion 110, though in some embodiments one or both of engagement tabs 115 extend at an angle to the plane of blade engagement portion 110.

Engagement tabs 115 are flexible so as to be able to occupy a natural, unflexed or undeflected configuration where the distal ends of engagement tabs 115 extend beyond the sides of blade engagement portion 110. Engagement tabs 115 are also configured to flex or deflect toward blade engagement portion 110 so as to occupy a second configuration that brings their respective distal ends closer toward the sides of blade engagement portion 110 or, in other words, in line with the sides of blade engagement portion 110.

Engagement tabs 115 may comprise the same material as the rest of blade engagement portion 110 or may comprise a distinct material. The material of engagement tabs 115 is preferably a flexible or elastically deformable material. Suitable materials include titanium and steel or alloys thereof as well as one or more plastics or polymers.

FIG. 1A illustrates blade extender 100 with two engagement tabs 115, though a skilled artisan will understand that only one locking tab would be required to achieve many of the functional advantages ascribed to blade extender 100. Similarly, although engagement tabs 115 are shown as being symmetrically placed on each side of blade engagement portion 110, the tabs may be placed other than symmetrically. Also, in this illustrated embodiment, engagement tabs 115 lie in the same plane as blade engagement portion 110 and further flex or deflect in that same plane. However, in some embodiments, engagement tabs 115 lie in a different plane from blade engagement portion 110 and/or flex or deflect in a distinct plane.

Blade engagement portion 110, as illustrated embodiment in FIG. 1B, further includes a driver locking tab 120 configured to releasably engage a driver as will be discussed in greater detail below. Similar to engagement tabs 115, driver locking tab 120 is flexible or deflectable. In its relaxed or non-deflected state, locking tab 120 lies substantially in the same plane as blade engagement portion 110, though locking tab 120 includes a projection 125 (also illustrated in FIG. 3B) extending out of that plane. As will be discussed in greater detail below, projection 125 is configured to engage with a driver that may be used to insert blade extender 100 into a surgical corridor, manipulate blade extender 100 within the corridor to move tissue to the side of the corridor, and to secure blade extender 100 to a retractor blade. Further, in some cases, it will be desirable to drive blade extender 100 into an intradiscal space to help anchor the retractor blade in position relative to the disc space. In some embodiments, projection 125 is configured to engage with depressions in the channel of the retractor blade, thereby fixing blade extender 100 relative to the retractor blade. Such a configuration may be particular useful when blade extender 100 is used as a temporary anchor for the retractor blade. Such depressions may be located along a midline of the channel on the retractor blade, or they may be positioned elsewhere in the channel, such as one either or both sides and even positioned along one or both edges of the channel. Such alternative positions may require a complimentary configuration of locking tab 120 and/or projection 125.

In some embodiments, engagement tabs 115 may serve the function of locking tab 120/projection 125. For example, where the depressions mentioned above are positioned along one or both edges of the channel in the retractor blade, the respective tips of engagement tabs 115 may be configured to engage the depressions, thereby not only maintaining blade device 100 within the channel but also fixing or at least partially fixing its longitudinal position in the channel. In some embodiments, such an arrangement may allow for blade device 100 to translate distally in a passive manner while preventing proximal translation.

As with engagement tabs 115, locking tab 120 may comprise the same material as or a distinct material from the rest of blade engagement portion 110. The material of locking tab 120 is preferably a flexible or elastically deformable material. Suitable materials include titanium and steel or alloys thereof as well as one or more plastics or polymers.

Blade extender 100 may be provided in a number of suitable lengths and sizes. A minimum length may be no more than the length required for the blade engagement portion 110 to function properly, which in some embodiments is from 2 cm to about 5 cm. In some embodiments, the total length of blade extender 100 (or 100A) is from about 2 cm to about 10 cm. In some embodiments, the total length of blade extender 100 is about 5 cm, about 6 cm, about 7 cm, or about 8 cm. The relative lengths of blade engagement portion 110 and elongate portion 105 may be about the same, though in some embodiments, the respective lengths are not the same. For example, in some embodiments, the ratio of the length of elongate portion 105 to the length of engagement portion 110 is greater than 1:2, such as about 1:1, about 1.5:1, about 2:1, or any suitable ratio between those values.

The width of blade extender 100 may be roughly consistent along its length from the proximal end of blade engagement portion 110 to the distal end of elongate portion 105; however, the width need not be consistent. The width of blade engagement portion 110 is generally chosen based on the width of the channel in a retractor blade or based on the restraining geometry of the retractor blade. For example, the width of blade engagement portion 110 may be substantially smaller or substantially larger than the width of elongate portion 105. However, whatever the relative widths are, the width of blade engagement portion 110 will generally be less than the width of the channel of the retractor blade; however, the width of engagement tabs 115 will generally be greater than the width of the retractor blade channel when the engagement tabs 115 are in their relaxed or undeflected state.

As has been discussed somewhat already, blade extender 100 may be used to achieve any number of purposes and may be modified to achieve those purposes. Tissue shim 100A is just one example of a modified version able to engage a retractor blade in the same manner as blade extender 100 but shaped distinctly to block a larger surface area of tissue. Within these two disclosed configurations there exist any number of modifications to shape and size. One such modification is the inclusion of a hook-shaped feature at the distal end of the device. Such a hook-shaped feature may be useful for pulling back tissue in the surgical corridor either to help establish the corridor or to reestablish the corridor.

The ability to disengage the device, whether it be an extender or a shim or some other variation, during a procedure without having to remove the device from the surgical corridor is considered to be one of the greatest benefits of these devices. Additionally, the ability to adjust the depth of the devices as retractor blades are opened or otherwise adjusted is also considered to be an advantageous feature not necessarily known in the art. Such functionality is enhanced with the use of a driver as discussed below.

FIGS. 4A and 4B illustrate a driver 200 coupled to blade extender 100. Driver 200 has a distal end 205 configured to receive at least a portion of blade extender 100. In this illustrated configuration, blade engagement portion 110 slides into an opening at distal end 205. In that distal opening, projection 125 of locking tab 120 engages driver 200 to maintain blade extender 100 in a fixed position in driver 200 but leaving engagement tabs 115 exposed so as to engage the channel of a retractor blade as discussed in further detail below.

Similar to blade extender 100, driver 200 has laterally projecting engagement tabs 215 that, like engagement tabs 115, are configured to engage the channel of a retractor blade. In this illustrated embodiment, engagement tabs 215 lie in substantially the same plane as driver 200, but, in some embodiments, one or both of engagement tabs 215 are angled relative the plane of driver 200. Engagement tabs 215 are useful to help properly position blade extender 100 in a retractor blade channel. Once positioned, driver 200 is disengaged from blade extender 100 to leave blade extender 100 in a retractor blade (as illustrated in FIGS. 5A and 5B). In some embodiments, however, driver 200 does not include any locking tabs.

Driver 200 includes a handle 210 at its proximal end and a shaft 220 running from handle 210 toward the distal end of driver 200. Handle 210, in this illustrated embodiment, has a lumen into which shaft 220 extends. Spring 230 is configured to maintain tension on shaft 220 to keep is pressed into handle 210. Handle 210 is configured to switch between a locked position and an unlocked position. In the locked position, driver 200 may receive impaction blows on its proximal end and transfer the energy from those blows directly to the blade extender 100 at the distal end. For example, if a surgeon desires to advance blade extender 100 into a disc space, a hammer or slap hammer may be used to gently pound against handle 210. And when removing blade extender 100 from a disc space, handle 210 is configured to receive a slap hammer to facilitate pulling forces.

In the unlocked position, handle 210 can be translated distally causing shaft 220 to, in turn, translate distally. Distal end of shaft 220 is configured to engage with projection 125 of locking tab 120. When shaft 220 translates distally, its distal end deflects locking tab 120 causing projection 125 to disengage from the distal end of the housing of driver 200, thereby allowing blade extender 100 (or tissue shim 100A or other suitable device) to be removed from driver 200.

FIGS. 5A and 5B illustrate blade extender 100 coupled to or engaged with a retractor blade 300 that includes a channel 305 that runs from the proximal end of retractor blade 300 toward the distal end without extending all the way to the distal end. In other words, channel 305 is closed at the distal end such that a device, such as blade extender 100 translating along channel 305 could not exit the channel at the distal end but could be withdrawn at the proximal end. However, in some embodiments, channel 305 is open at the distal end.

FIG. 5A illustrates that engagement tabs 115 extend into the lateral sides of channel 305. In this configuration, engagement tabs 115 may be sized and designed to be in their resting or undeflected state when in channel 305. Though, in some embodiments, even when engagement tabs 115 extend into the lateral sides of channel 305, they are still at least partially deflected, which may be useful for fixing blade extender 100 in place relative to retractor blade 300.

FIG. 5A also illustrates that in this illustrated embodiment elongate portion 105 extends beyond the distal end of retractor blade 300 when blade engagement portion 110 is at the distal-most position of channel 305. The amount that elongate portion 105 extends beyond the distal end of retractor blade 300 is a function of the length of elongate portion 105 as well as the distance between the distal end of retractor blade 300 and the distal end of channel 305. Although elongate portion 105 need not extend any distance beyond the distal end of retractor blade 300, in some embodiments, the distance beyond the distal end of retractor blade 300 is from about 0.1 cm to about 5 cm. In some embodiments, that distance is about 1 cm, about 2 cm, about 3 cm, about 4 cm, or any value there between.

FIG. 5B illustrates that channel 305 is defined not only as a depression in one side of retractor blade 300 but further includes a lateral lip 310 along each edge of the depression. The shape of channel 305 along with lateral lip 310, as illustrated, is somewhat rounded; however, a square or rectangular shape could also be used. Also, channel 305 need not have a substantially flat surface at the bottom of the depression. In some embodiments, channel 305 is more rounded; however, channel 305 should still include lateral lip 310 if it is to be able to retain blade extender 100.

Figure 6:
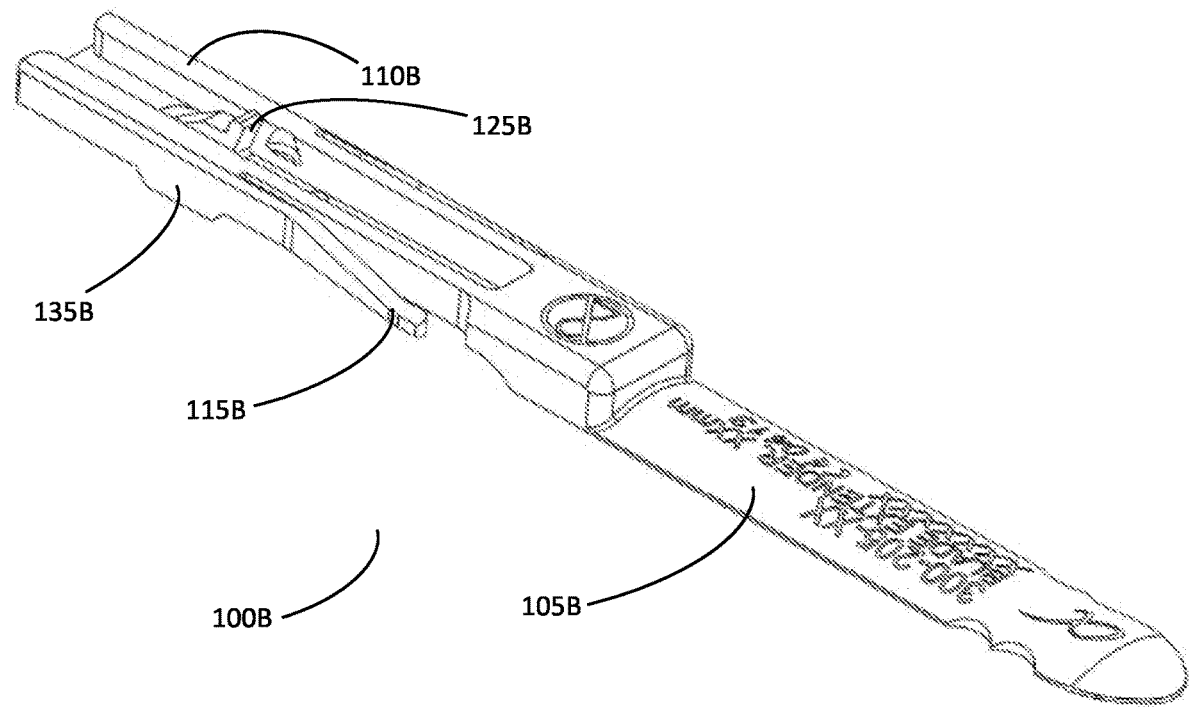
FIG. 6 is a perspective view of another embodiment of retractor blade device according to the present disclosure.

FIG. 6 illustrates another variation on blade extender 100, which is blade extender 100B. Similar to blade extender 100, blade extender 100B includes an elongate portion 105B and a blade engagement portion 110B having two engagement tabs 115B and a locking tab (not visible in this view) with a projection 125B. The function of these features will be largely similar to the function of the corresponding features of blade extender 100 as discussed herein as would be readily apparent to a skilled artisan. However, blade extender 100B includes a pair of tabs or ribs 135B that extend downward or backward from blade engagement portion 110B.

Figure 7:
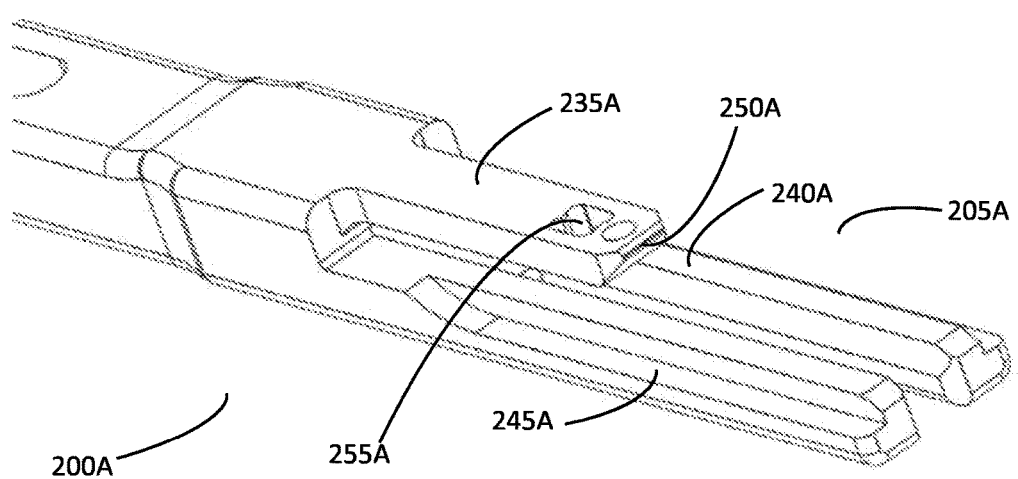
FIG. 7 is a perspective view of a distal end of another embodiment of a deployment instrument according to the present disclosure.

FIG. 7 illustrates a distal portion of a variation on driver 200, which is referred to as driver 200A, the distal end of which is labeled as 205A. Distal end 205A comprises three extensions or prongs 235A, 240A, and 245A. Extension 235A includes at its distal end a sloped surface 250A and, proximal of sloped surface 250A an opening 255A. When blade extender 100B is received by driver 200A, opening 255A receives projection 125B so as to hold blade extender 100B in a locked orientation relative to driver 200A. In this illustrated embodiment, opening 255A is a through-hole extending completely through extension 235A; however, in some embodiments, the functionality of opening 255A may be achieved with a notch or a cutout on the underside of extension 235A.

Each of extensions 240A and 245A includes an outward-facing cutout configured to receive downward-facing tabs 135B of blade extender 100B. This design provides greater stability to blade extender 100B when it is secured within driver 200A.

Figure 8:
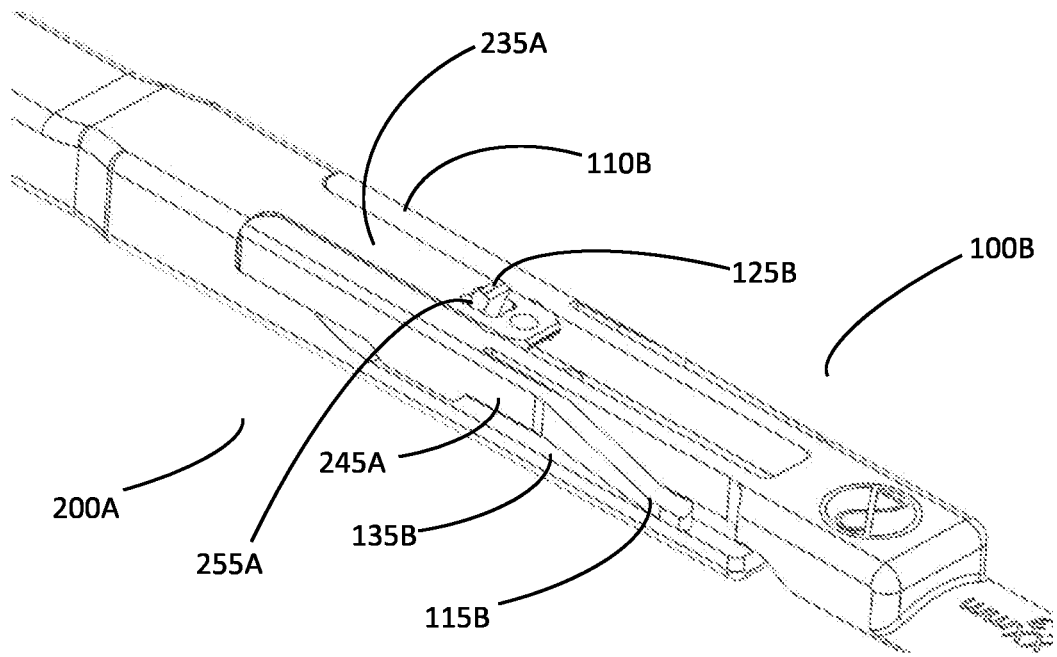
FIG. 8 is an enlarged view of a portion of the deployment instrument of FIG. 7 engaged with the retractor blade device of FIG. 6.

FIG. 8 illustrates the engagement between driver 200A and blade extender 100B. Blade extender 100B is secured to driver 200A by sliding blade engagement portion 110B into distal end 205A of driver 200A. A locked arrangement is achieved when blade extender 100B is advanced far enough that projection 125B is received by opening 255A. In some embodiments, both extension 235A and the locking tab of blade extender 100B are comprised of one or more resilient materials that at least partially deflect when subject to a certain amount of pressure.

Driver 200A includes a shaft (similar to shaft 220) that is configured to be translatable along an axis defined by driver 200A. The tip of the shaft applies a deflecting force to extension 235A and/or the locking tab of blade extender 100B so as to cause projection 125B to be released from opening 255A, thereby allowing blade extender 100B to be released from driver 200A.

Figure 9:
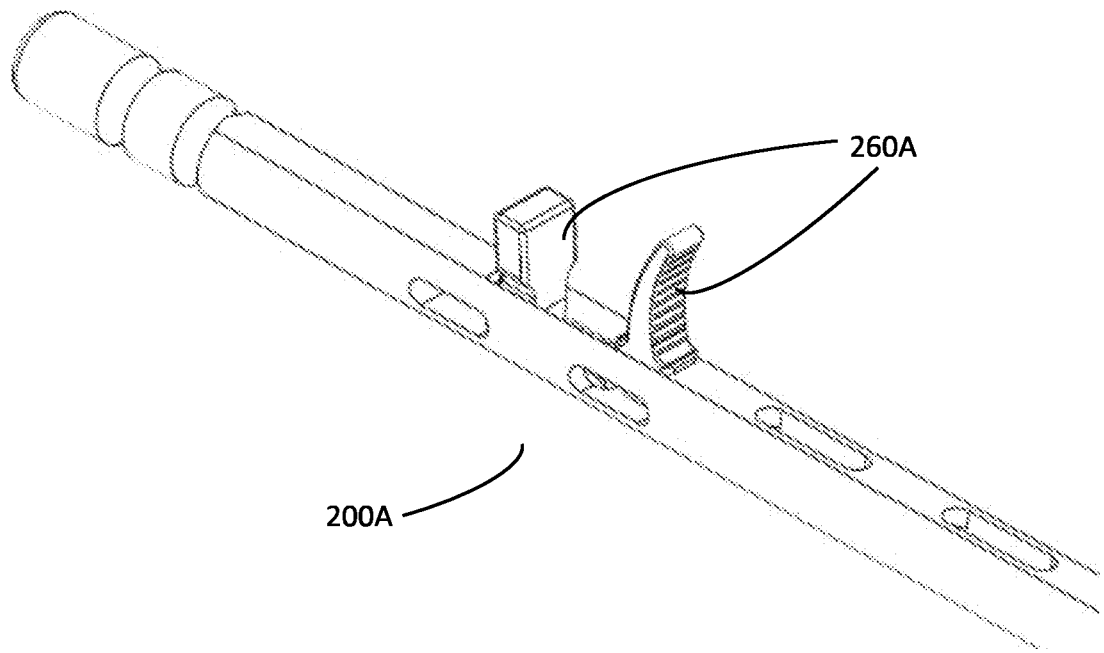
FIG. 9 is a perspective view of a proximal end of the deployment instrument of FIG. 7.

FIG. 9 illustrates the proximal end of driver 200A, which includes a trigger or release mechanism 260A that is configured to manipulate the shaft contained within driver 200A so as to control the release of blade extender 100B from driver 200A.

During a surgical procedure, a retractor assembly having at least one retractor blade is typically used to create a surgical corridor to reach a surgical site. A suitable method of utilizing extender blade 100 may include, first, advancing at least one retractor blade toward a surgical site so as to begin creating a surgical corridor to access a surgical site. A surgeon may desire to use a blade extender such as those disclosed herein to further stabilize the surgical corridor. This may be accomplished when first establishing the surgical corridor if the surgical corridor requires a depth greater than the length of the retractor blades. The blade extender may be advanced along a channel of the retractor blade, or the extender may be advanced directly into the surgical corridor and then, when ready to be affixed to the retractor blade, moved directly into the retractor blade's channel by pressing the extender into the channel in a direction perpendicular to the axis or plane of the channel.

Additionally, in some embodiments, the blade extenders disclosed herein may be advanced into an intradiscal space to temporarily anchor the retractor blade relative to the disc space.

The blade extenders disclosed herein may alternatively be used to restore a surgical corridor without the need to reposition the retractor blade, for example if tissue has crept around or under the retractor blades. In such a scenario, a suitable blade extender, such as blade extender 100, is advanced into the surgical corridor, and the elongate portion 105 is used to push or pull back the errant tissue. Advancing blade extender 100 and manipulating it in the surgical corridor may be accomplished by first coupling blade extender 100 to a suitable driver, such as driver 200. Blade extender 100 may also include a hook-shaped feature at its distal end or some other curvature or feature to grab errant tissue to pull it out of the surgical corridor.

In addition to using blade extender 100 (or 100A or 100B) to clear the surgical corridor, blade extender 100 may further maintain the surgical corridor. This is achieved while holding back the tissue. A surgeon inserts blade engagement portion 110 into a channel of the retractor blade, such as channel 305, which may be achieved by advancing blade extender along channel 305 or by inserting blade extender 100 into channel 305 at a point toward the distal end of channel 305. Pressing blade engagement portion 110 into channel 305 causes engagement tabs 115 to bend or deflect inward allowing blade engagement portion 110 to seat in channel 305. When fully seated, engagement tabs 115 at least partially expand to fill the space between the sides of blade engagement portion 110 and the sides of channel 305. If driver 200 is used to engage blade extender 100 in retractor blade 300, driver 200 may also be inserted into channel 305, and, if engagement tabs 215 are present, by forcing engagement tabs 215 to compress or bend inwardly to allow driver 200 to pass into channel 305.

With blade extender 100 properly positioned in channel 305, driver 200 is disengaged from blade extender 100 to be translated proximally along channel 305 leaving blade extender 100 in place in retractor blade 300. This disengagement is achieved by rotating locking ring 210.

Removal of blade extender 100 may be achieved by reinserting driver 200 into the proximal end of channel 305 and translating distal end 205 along channel 305 until distal end 205 engages with blade engagement portion 110 of blade extender 100. When projection 125 engages with the locking mechanism of driver 200 contained within distal end 205, driver 200 may then be translated proximally pulling blade extender 100 along with it and out of the surgical corridor.

This removal process may be used to readjust tissue within the surgical corridor, in which case, blade extender 100 may be again inserted into channel 305 after tissue in the corridor has been pulled to the side or the surgical site has been otherwise unobstructed.

In some embodiments, blade extender 100, tissue shim 100A, or some other suitable device that is consistent with the present disclosure is used to enhance the functionality of the retractor system with which these devices are used. For example, some retractor systems include retractor blades whose length is adjustable. Such adjustable blades may be bulky or complicated, and using the devices disclosed herein with a simple, non-adjustable blade results in essentially an adjustable blade that is not bulky or complicated.

Some retractor systems utilize releasable blades of different lengths and/or shapes instead of having adjustable blades. However, that solution requires the system to include many different blades, which increases manufacturing costs, transportation costs, etc. The use of the devices disclosed herein obviates the need for blades of different lengths because a single blade can achieve different lengths and even shapes if the devices disclosed herein are used. Moreover, the devices disclosed herein may be single-use or disposable.

Some retractor systems have complex mechanisms that allow the retractor blades to achieve a "level toe" movement as the blades are expanded. This is achieved by incrementally increasing the length of the blade as it is toed out, thereby minimizing the chance that tissue could creep under the blade tip as it is toed out. However, the present devices can be used to achieve a "level toe" movement by distally advancing the device—such as blade extender 100 or tissue shim 100A—along the retractor blade as the blade or blades are toed out.

EMBODIMENTS

The following embodiments are provided as examples only of specific configurations, materials, arrangements, etc. contemplated by the authors of this disclosure:

Embodiment 1. A retractor blade device comprising:
a retractor blade engagement portion having a body portion with a distal end and a proximal end, the retractor blade engagement portion configured to sit at least partially in a channel of a retractor blade, the body portion having a first retention component extending therefrom; and
an extension portion having a distal end and a proximal end.

Embodiment 2. The retractor blade device of embodiment 1, wherein the extension portion is substantially flat or curved.

Embodiment 3. The retractor blade device of embodiment 1 or 2, wherein the extension portion has a hook feature.

Embodiment 4. The retractor blade device of embodiment 1, 2, or 3, wherein the extension portion is wider than the retractor blade engagement portion.

Embodiment 5. The retractor blade device of embodiment 1, 2, 3, or 4, wherein at least a portion of the extension portion extends laterally of the blade engagement portion.

Embodiment 6. The retractor blade device of embodiment 1, 2, 3, 4, or 5, wherein the distal end of the extension portion extends beyond the distal end of the blade engagement portion by at least about 1 cm, at least about 2 cm, at least about 3 cm, or at least about 4 cm.

Embodiment 7. The retractor blade device of embodiment 1, 2, 3, 4, 5, or 6, wherein the proximal end of the extension portion is positioned at any one of the following positions relative to the proximal and distal ends of the blade engagement portion: (a) proximally of the proximal end; (b) substantially in line with the proximal end; (c) substantially in line with the distal end; or (d) at a point between the proximal and distal ends.

Embodiment 8. The retractor blade device of embodiment 1, 2, 3, 4, 5, 6, 7, wherein the body portion defines a first plane, wherein the extension portion defines a second plane, and wherein the first and second planes are parallel to each other.

Embodiment 9. The retractor blade device of embodiment 8, wherein the first and second planes are not coplanar.

Embodiment 10. The retractor blade device of embodiment 1, 2, 3, 4, 5, 6, 7, 8, or 9, further comprising a second retention component.

Embodiment 11. The retractor blade device of embodiment 10, wherein the first retention component and/or the second retention component comprises a resilient projection.

Embodiment 12. The retractor blade device of embodiment 10 or 11, wherein the first retention component and/or the second retention component extends in a plane coplanar with the body portion.

Embodiment 13. The retractor blade device of embodiment 10, 11, or 12, wherein the first retention component and/or the second retention component is configured to engage at least a portion of a channel of a retractor blade.

Embodiment 14. The retractor blade device of embodiment 10, 11, 12, or 13, wherein the first retention component and/or the second retention component is configured to allow the retractor blade device to be brought into the channel from a position perpendicular to a plane defined by the channel.

Embodiment 15. The retractor blade device of embodiment 1, 2, 3, 4, 5, 6, 7, 8, 9, 10, 11, 12, 13, or 14, wherein the distal end of the extension portion has a rounded profile.

Embodiment 16. The retractor blade device of embodiment 1, 2, 3, 4, 5, 6, 7, 8, 9, 10, 11, 12, 13, 14, or 15, wherein the extension portion comprises at least one scalloped edge.

Embodiment 17. The retractor blade device of embodiment 1, 2, 3, 4, 5, 6, 7, 8, 9, 10, 11, 12, 13, 14, 15, or 16, wherein the body portion further comprises a driver locking mechanism.

Embodiment 18. The retractor blade device of embodiment 17, wherein the driver locking mechanism comprises a resilient portion and a projection.

Embodiment 19. The retractor blade device of embodiment 18, wherein the projection is configured to engage a depression in a retractor blade.

Embodiment 20. The retractor blade device of embodiment 18 or 19, wherein the resilient portion lies substantially in the same plane as the body portion.

Embodiment 21. The retractor blade device of embodiment 18, 19, or 20, wherein the projection extends from a plane defined by the body portion.

Embodiment 22. The retractor blade device of embodiment 1, 2, 3, 4, 5, 6, 7, 8, 9, 10, 11, 12, 13, 14, 15, 16, 17, 18, 19, 20, or 21, wherein the extension portion comprises a channel or track extending from a point near the proximal end of the extension portion toward the distal end of the extension portion.

Embodiment 23. The retractor blade device of embodiment 22, wherein the channel or track is open at its proximal end and/or open at its distal end.

Embodiment 24. The retractor blade device of embodiment 1, 2, 3, 4, 5, 6, 7, 8, 9, 10, 11, 12, 13, 14, 15, 16, 17, 18, 19, 20, 21, 22, or 23, wherein the body portion further comprises at least one tab extending therefrom.

Embodiment 25. The retractor blade device of embodiment 24, wherein the tab extends in a direction distinct from the direction in which the retention component extends.

Embodiment 26. The retractor blade device of embodiment 25, wherein the direction of the tab is normal to the direction of the retention component.

Embodiment 27. A blade device driver configured to engage a retractor blade device, the blade device driver comprising:
a handle;
an elongated housing;
a shaft contained within the housing; and
a receiving portion configured to receive at least a portion of the retractor blade device;
wherein the handle communicates with the shaft to releasably engage the retractor blade device.

Embodiment 28. The blade device driver of embodiment 27, wherein the retractor blade device is the retractor blade device of embodiment 1, 2, 3, 4, 5, 6, 7, 8, 9, 10, 11, 12, 13, 14, 15, 16, 17, 18, 19, 20, 21, 22, 23, 24, 25, or 26.

Embodiment 29. The blade device driver of embodiment 28, wherein the receiving portion comprises a distal opening in the housing configured to receive at least a portion of the body portion of the retractor blade device.

Embodiment 30. The blade device driver of embodiment 28 or 29, wherein the blade device driver is configured to releasably engage the driver locking mechanism of the retractor blade device.

Embodiment 31. The blade device driver of embodiment 27, 28, 29, or 30, wherein the housing comprises a first retention component configured to retain the blade device driver in a channel of a retractor blade.

Embodiment 32. The blade device driver of embodiment 31, wherein the housing comprises a second retention component configured to retain the blade device driver in the channel.

Embodiment 33. The blade device driver of embodiment 31 or 32, wherein the first retention component and/or the second retention component is configured to allow the blade device driver to be brought into the channel from a position perpendicular to a plane defined by the channel Embodiment 34. The blade device driver of embodiment 28, 29, 30, 31, 32, or 33, wherein the handle is configured to occupy a locked position that allows compaction forces to be transferred from the handle through the housing and directly to the retractor blade device.

Embodiment 35. The blade device driver of embodiment 28, 29, 30, 31, 32, 33, or 34, wherein the receiving portion comprises three extensions: a locking extension and two receiving extensions—the locking extension configured to receive the driver locking mechanism of a retractor blade device and at least one of the two receiving extensions having a groove along at least portion of its length, the groove configured to receive the at least one tab of a retractor blade device.

Embodiment 36. The blade device driver of embodiment 35, wherein the three extensions of the receiving portion are parallel to each other.

Embodiment 37. The blade device driver of embodiment 27, 28, 29, 30, 31, 32, 33, 34, 35, or 36, wherein the handle comprises a trigger release mechanism that extends away from an axis defined by the shaft.

Embodiment 38. A retractor blade kit comprising:
a retractor blade defining a plane and having a proximal end and a distal end with a channel extending from the proximal end toward the distal end; and
a retractor blade device, at least a portion of the retractor blade device configured to engage with the channel of the retractor blade;
wherein the retractor blade device is configured to be engaged with the channel by inserting at least a portion of the retractor blade device into the channel at a point away from the proximal end of the retractor blade.

Embodiment 39. The retractor blade kit of embodiment 38, wherein the retractor blade device is the retractor blade device of embodiment 1, 2, 3, 4, 5, 6, 7, 8, 9, 10, 11, 12, 13, 14, 15, 16, 17, 18, 19, 20, 21, 22, 23, 24, 25, or 26.

Embodiment 40. The retractor blade kit of embodiment 38 or 39, wherein the channel is closed at the distal end of the retractor blade.

Embodiment 41. The retractor blade kit of embodiment 38, 39, or 40, wherein the channel is open at the proximal end of the retractor blade.

Embodiment 42. The retractor blade kit of embodiment 41, wherein the retractor blade device is further configured to be engaged with the channel by inserting at least a portion of the retractor blade device into the channel by accessing the opening of the channel at the proximal end of the retractor blade.

Embodiment 43. The retractor blade kit of embodiment 38, 39, 40, 41, or 42, further comprising a blade device driver configured to engage with at least a portion of the retractor blade device, wherein the blade device driver is further configured to manipulate the movement of the retractor blade device and engage the retractor blade device with the channel of the retractor blade.

Embodiment 44. The retractor blade kit of embodiment 43, wherein the blade device driver is the blade device driver of embodiment 27, 28, 29, 30, 31, 32, 33, 34, 35, 36, or 37.

Embodiment 45. A method of using a retractor blade device, the method comprising:
engaging the retractor blade device with a channel of a retractor blade by inserting at least a portion of the retractor blade device into the channel at a point distal to a proximal end of the channel.

Embodiment 46. The method of embodiment 45, wherein the retractor blade device is the retractor blade device of embodiment 1, 2, 3, 4, 5, 6, 7, 8, 9, 10, 11, 12, 13, 14, 15, 16, 17, 18, 19, 20, 21, 22, 23, 24, 25, or 26.

Embodiment 47. The method of embodiment 45 or 46, wherein engaging the retractor blade device with the channel of the retractor blade comprises moving the at least a portion of the retractor blade device in a direction normal to a plane defining the channel.

Embodiment 48. The method of embodiment 45, 46, or 47, wherein engaging the retractor blade device with the channel of the retractor blade comprises engaging at least a portion of the retractor blade device with one or more depressions in the channel of the retractor blade.

Embodiment 49. The method of embodiment 45, 46, 47, or 48, wherein the retractor blade is positioned within a surgical opening of a patient so as to create a surgical corridor prior to the retractor blade device being engaged with the channel on the retractor blade.

Embodiment 50. The method of embodiment 49, further comprising sweeping the surgical corridor and/or a surgical site of interfering tissue with the retractor blade device prior to the retractor blade device being engaged with the channel of the retractor blade.

Embodiment 51. The method of embodiment 45, 46, 47, 48, 49, or 50, wherein the retractor blade and the retractor blade device comprise the retractor blade kit of embodiment 38, 39, 40, 41, 42, 43, or 44.

Embodiment 52. The method of embodiment 45, 46, 47, 48, 49, 50, or 51, wherein a blade device driver is used to insert the retractor blade device into the surgical corridor, manipulate the movement of the retractor blade device in the surgical corridor, and engage the retractor blade device with the channel of the retractor blade.

Embodiment 53. The method of embodiment 52, wherein the blade device driver is the blade device driver of embodiment 27, 28, 29, 30, 31, 32, 33, 34, 35, 36, or 37.

Embodiment 54. The method of embodiment 45, 46, 47, 48, 49, 50, 51, 52, or 53, further comprising toeing out the retractor blade while simultaneously advancing the retractor blade device distally along the channel of the retractor blade.

Embodiment 55. The method of embodiment 52, 53, or 54, further comprising detaching the blade device driver from the retractor blade device so as to leave the retractor blade device in the channel of the retractor blade while removing the blade device driver from the surgical corridor.

Embodiment 56. The method of embodiment 55, wherein removing the blade device driver from the surgical corridor comprising sliding the blade device driver proximally along the channel of the retractor blade and out a proximal opening of the channel.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. In some embodiments, the terms "about" and "approximately" refer to numerical parameters within 10% of the indicated range.

The terms "a," "an," "the," and similar referents used in the context of describing the embodiments of the present disclosure (especially in the context of any claimed invention) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the author(s) of this disclosure for carrying out the disclosed embodiments. Of course, variations on these described embodiments will become apparent to those of ordinary skill in the art upon reading the foregoing description. The author(s) expects skilled artisans to employ such variations as appropriate, and the author(s) intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

Furthermore, if any references have been made to patents and printed publications throughout this disclosure, each of these references and printed publications are individually incorporated herein by reference in their entirety.

In closing, it is to be understood that the embodiments disclosed herein are illustrative of the principles of the present disclosure. Other modifications that may be employed are within the scope of this disclosure. Thus, by way of example, but not of limitation, alternative configurations of the embodiments of the present disclosure may be utilized in accordance with the teachings herein. Accordingly, the present disclosure is not limited to the embodiments precisely as shown and described.

The invention claimed is:

1. A retractor blade device comprising:
   a retractor blade engagement portion having a body portion with a distal end and a proximal end, the retractor blade engagement portion configured to sit at least partially in a channel of a retractor blade, the body portion having first and second retention components comprising resilient projections, each component extending laterally therefrom to engage respective lateral edges of the channel; and
   an extension portion having a distal end and a proximal end;
   wherein the first and second retention components extend in a plane coplanar with the body portion; and
   wherein the first and second retention components are configured to allow the retractor blade device to be brought into the channel from a position perpendicular to a place defined by the channel.

2. The retractor blade device of claim 1, wherein the extension portion has a hook feature.

3. The retractor blade device of claim 1, wherein the extension portion is wider than the retractor blade engagement portion.

4. The retractor blade device of claim 1, wherein at least a portion of the extension portion extends laterally relative to the blade engagement portion.

5. The retractor blade device of claim 1, wherein the body portion defines a first plane, wherein the extension portion defines a second plane, and wherein the first and second planes are parallel to each other.

6. The retractor blade device of claim 5, wherein the first and second planes are not coplanar.

7. The retractor blade device of claim 1, wherein the extension portion comprises at least one scalloped edge.

8. The retractor blade device of claim 1, wherein the body portion further comprises a driver locking mechanism.

9. The retractor blade device of claim 8, wherein the driver locking mechanism comprises a resilient portion and a projection.

10. The retractor blade device of claim 9, wherein the projection is configured to engage a depression in a retractor blade.

11. The retractor blade device of claim 10, wherein the resilient portion lies substantially in the same plane as the body portion.

12. The retractor blade device of claim 11, wherein the projection extends from a plane defined by the body portion.

13. The retractor blade device of claim 1, wherein the extension portion comprises a channel or track extending from a point near the proximal end of the extension portion toward the distal end of the extension portion.

14. The retractor blade device of claim 13, wherein the channel or track is open at its proximal end.

15. The retractor blade device of claim 1, wherein the body portion further comprises at least one tab extending therefrom.

16. The retractor blade device of claim 15, wherein the tab extends in a direction distinct from the direction in which the retention components extend.

17. The retractor blade device of claim 16, wherein the direction of the tab is normal to the direction of the retention components.

18. The retractor blade device of claim 1, wherein the extention portion includes a curved surface.

19. The retractor blade device of claim 18, wherein the curved surface curves in a direction away from a plane defined by retractor blade engagement portion.

20. The retractor blade device of claim 18, wherein the extention portion includeds a second channel extending in the same direction as the channel of the retractor blade but defining a plane that is not coplanar with the channel of the retractor blade.

* * * * *